United States Patent
Rajaraman et al.

(10) Patent No.: US 9,658,179 B2
(45) Date of Patent: May 23, 2017

(54) SYSTEM AND METHOD FOR A MEMS TRANSDUCER

(71) Applicant: Infineon Technologies AG, Neubiberg (DE)

(72) Inventors: Vijaye Kumar Rajaraman, Villach (AT); Yonsuang Arnanthigo, Villach (AT); Alfons Dehe, Reutlingen (DE); Stefan Kolb, Unterschleissheim (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 14/749,102

(22) Filed: Jun. 24, 2015

(65) Prior Publication Data

US 2016/0377569 A1 Dec. 29, 2016

(51) Int. Cl.
*G01N 27/22* (2006.01)
*B81C 1/00* (2006.01)
*B81B 3/00* (2006.01)

(52) U.S. Cl.
CPC ......... *G01N 27/223* (2013.01); *B81B 3/0018* (2013.01); *B81C 1/00166* (2013.01)

(58) Field of Classification Search
CPC ......... H01L 27/16; H01L 37/00; H01L 29/84; B81C 1/00; B81C 1/00166; B81B 3/00; B81B 3/0018; G01N 27/22; G01N 27/223
USPC ....................................................... 257/416
See application file for complete search history.

(56) References Cited

U.S. PATENT DOCUMENTS

| | | | |
|---|---|---|---|
| 4,761,710 A | 8/1988 | Chen | |
| 4,965,698 A | 10/1990 | Thoma et al. | |
| 6,173,602 B1* | 1/2001 | Moseley | G01N 27/125 422/88 |
| 6,690,569 B1 | 2/2004 | Mayer et al. | |
| 7,340,952 B2 | 3/2008 | Tanida | |
| 8,354,729 B2 | 1/2013 | Hsieh et al. | |
| 8,650,953 B2 | 2/2014 | Cherian et al. | |
| 8,683,847 B2 | 4/2014 | Moon et al. | |
| 8,707,781 B2 | 4/2014 | Humbert et al. | |
| 8,721,970 B2 | 5/2014 | Willett et al. | |
| 8,896,073 B2 | 11/2014 | Ponomarev et al. | |
| 2011/0072899 A1 | 3/2011 | Hoffmann et al. | |
| 2012/0032692 A1 | 2/2012 | Kothari et al. | |
| 2013/0075255 A1 | 3/2013 | Moon et al. | |
| 2013/0139587 A1 | 6/2013 | Le Neel et al. | |
| 2013/0160518 A1 | 6/2013 | Le Neel et al. | |
| 2013/0256825 A1 | 10/2013 | Humbert et al. | |

(Continued)

FOREIGN PATENT DOCUMENTS

EP 2230507 9/2010

*Primary Examiner* — Chuong A Luu
(74) *Attorney, Agent, or Firm* — Slater Matsil, LLP (57) ABSTRACT

According to an embodiment, a microelectromechanical systems (MEMS) transducer includes a substrate with a first cavity that passes through the substrate from a backside of the substrate. The MEMS transducer also includes a perforated first electrode plate overlying the first cavity on a topside of the substrate, a second electrode plate overlying the first cavity on the topside of the substrate and spaced apart from the perforated first electrode plate by a spacing region, and a gas sensitive material in the spacing region between the perforated first electrode plate and the second electrode plate. The gas sensitive material has an electrical property that is dependent on a concentration of a target gas.

22 Claims, 8 Drawing Sheets

(56) References Cited

U.S. PATENT DOCUMENTS

2014/0102172 A1 4/2014 Daamen et al.
2014/0208838 A1* 7/2014 Moon .................... G01N 27/16
　　　　　　　　　　　　　　　　　　　73/114.75

* cited by examiner

SYSTEM AND METHOD FOR A MEMS TRANSDUCER

TECHNICAL FIELD

The present invention relates generally to microfabricated structures, and, in particular embodiments, to a system and method for a microelectromechanical systems (MEMS) transducer.

BACKGROUND

Transducers convert signals from one domain to another and are often used as sensors. One common transducer used as a sensor and seen in everyday life is a microphone, which converts sound waves to electrical signals. Another example of a common sensor is a thermometer. Various transducers exist that serve as thermometers by transducing temperature signals into electrical signals.

Microelectromechanical systems (MEMS) based sensors include a family of transducers produced using micromachining techniques. MEMS, such as a MEMS microphone, gather information from the environment by measuring the change of physical state in the transducer and transferring a transduced signal to processing electronics that are connected to the MEMS sensor. MEMS devices may be manufactured using micromachining fabrication techniques similar to those used for integrated circuits.

MEMS devices may be designed to function as, for example, oscillators, resonators, accelerometers, gyroscopes, thermometers, pressure sensors, microphones, microspeakers, and micro-mirrors. As an example, many MEMS devices use capacitive sensing techniques for transducing the physical phenomenon into electrical signals. In such applications, the capacitance change in the sensor is converted into a voltage signal using interface circuits.

One such capacitive sensing device is a MEMS microphone. A MEMS microphone generally has a deflectable membrane separated by a small distance from a rigid backplate. In response to a sound pressure wave incident on the membrane, it deflects towards or away from the backplate, thereby changing the separation distance between the membrane and backplate. Generally, the membrane and backplate are made out of conductive materials and form "plates" of a capacitor. Thus, as the distance separating the membrane and backplate changes in response to the incident sound wave, the capacitance changes between the "plate" and an electrical signal is generated.

MEMS, such as capacitive MEMS for example, are often used in mobile electronics, such as tablet computers or mobile phones. In some applications, it may be desirable to provide sensors with new or increased functionality in order to provide additional or improved functionality to the electronic system, such as a tablet computer or mobile phone, for example.

SUMMARY

According to an embodiment, a microelectromechanical systems (MEMS) transducer includes a substrate with a first cavity that passes through the substrate from a backside of the substrate. The MEMS transducer also includes a perforated first electrode plate overlying the first cavity on a topside of the substrate, a second electrode plate overlying the first cavity on the topside of the substrate and spaced apart from the perforated first electrode plate by a spacing region, and a gas sensitive material in the spacing region between the perforated first electrode plate and the second electrode plate. The gas sensitive material has an electrical property that is dependent on a concentration of a target gas.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Description is made with respect to various embodiments in a specific context, namely gas transducers, and more particularly, MEMS humidity sensors. Some of the various embodiments described herein include MEMS transducers, MEMS microphones, MEMS gas sensors, MEMS humidity sensors, integrated MEMS microphone and humidity sensing systems, interface circuits for MEMS transducer systems, and integrated multiple transducer systems. In other embodiments, aspects may also be applied to other applications involving any type of sensor or transducer according to any fashion as known in the art.

As the number of connected devices in daily use has increased through rapid miniaturization in technology, advancements in mobile connectivity, and improvements in energy management and efficiency, the demand for additional functionality has also increased. One area of additional functionality is provided through the integration of additional sensors. Mobile devices, or devices in general, may include multiple sensors such as a microphone, an image sensor, an accelerometer, and a gyroscope, for example. Adding additional sensor types may be advantageous in some applications. However, in various applications, such as mobile devices for example, the space available for additional sensors may be limited by both the physical size of the device and the added cost of the additional sensors. Thus, the integration of additional sensors presents opportunities for innovation.

According to various embodiments described herein, a capacitive MEMS gas sensor is provided that is suitable for integration. A process for forming, for example, a MEMS microphone includes forming a perforated backplate and a deflectable membrane, spaced apart from the perforated backplate, over a cavity in a substrate. According to various embodiments, a similar process for forming a MEMS gas sensor with a similar structure includes forming a perforated first electrode and a second electrode, spaced apart from the perforated electrode, over a cavity in a substrate. In such embodiments, the spacing between the first electrode and the second electrode is filled with a gas sensitive dielectric material. In particular embodiments, the dielectric material is sensitive to humidity and a capacitive MEMS humidity sensor is produced. In various embodiments, the capacitive MEMS humidity sensor is integrated in a same substrate as a MEMS microphone. The layers of the backplate and membrane for the microphone may be formed simultaneously with the first electrode and the second electrode for the humidity sensor. Thus, various embodiments include an integrated capacitive MEMS gas sensor, e.g., a humidity sensor, which may increase the functionality of various devices.

Figure 1:
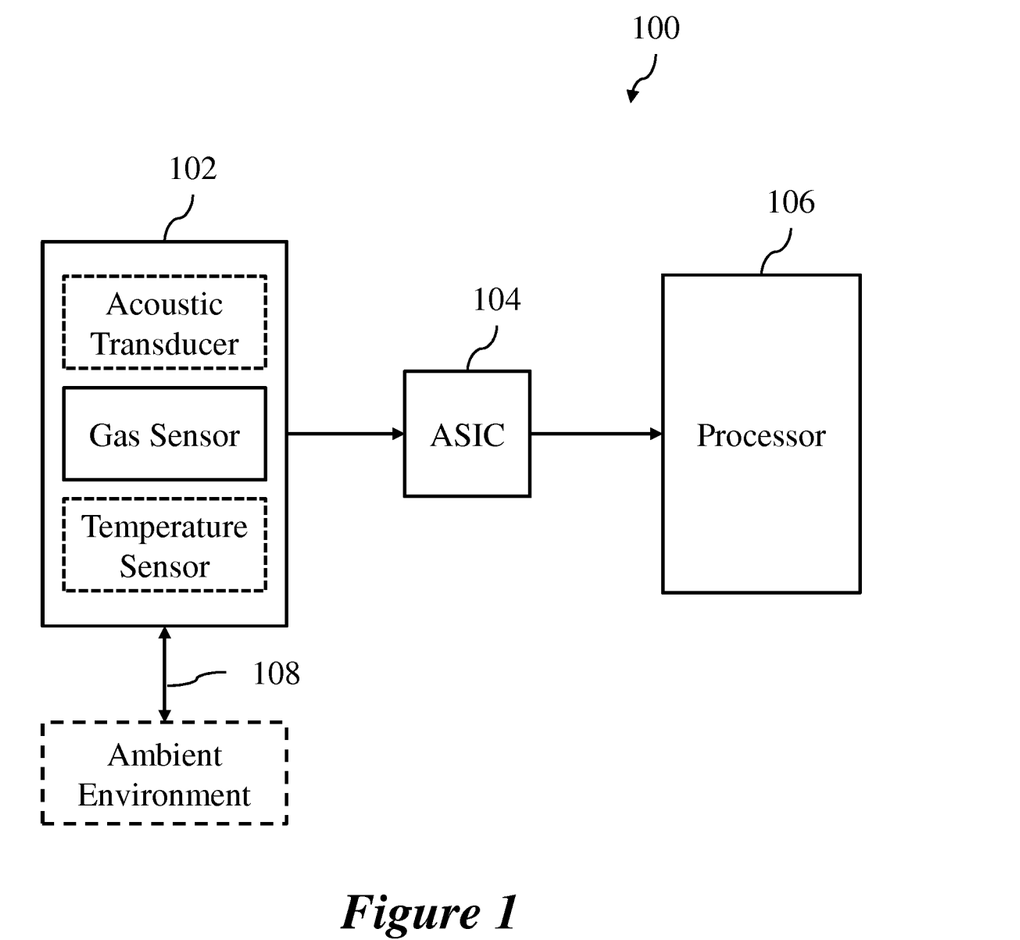
FIG. 1 illustrates a system block diagram of embodiment MEMS transducer system.

FIG. 1 illustrates a system block diagram of embodiment MEMS transducer system 100 including MEMS transducer 102, application specific integrated circuit (ASIC) 104, and processor 106. According to various embodiments, MEMS transducer 102 includes a gas sensor that transduces physical signals from gases in contact with MEMS transducer 102 into electrical signals that may be readout by ASIC 104 and processed by processor 106. In specific embodiments, the gas sensor of MEMS transducer 102 includes a humidity sensor that generates an electrical signal related to the humidity of the ambient environment of MEMS transducer 102.

According to various embodiments, MEMS transducer 102 may include multiple sensors integrated on a same semiconductor die. Specifically, MEMS transducer 102 includes an acoustic transducer, i.e., a microphone or a microspeaker, and a gas sensor in some embodiments, and may also include a temperature sensor in further embodiments (as shown). In some embodiments, the MEMS transducer 102 includes a capacitive MEMS humidity sensor and a capacitive MEMS microphone, both including first and second sensing electrodes that are formed of the same respective first and second layers in the semiconductor structure. Thus, in particular embodiments, the integration leads to small device size and simple fabrication.

In various embodiments, MEMS transducer 102 is coupled to the ambient environment through environmental coupling 108. For example, an opening or port, such as an acoustic port, may be provided in a device package (not shown) that includes MEMS transducer system 100. In such embodiments, the port provides environmental coupling 108 to the ambient environment of the device package including MEMS transducer system 100.

According to various embodiments, ASIC 104 includes an amplifier and bias circuit for interfacing MEMS transducer 102. ASIC 104 may also include an analog to digital converter (ADC) in some embodiments. In various embodiments, ASIC 104 may further include additional circuits to perform various additional functions related to interfacing, biasing, or processing electrical signals, for example. Further, MEMS transducer 102 includes an actuator, such as a microspeaker in some embodiments, and ASIC 104 includes driver circuits to driving the actuator. In some embodiments, ASIC 104 is formed on a same semiconductor die as MEMS transducer 102. In other embodiments, ASIC 104 is formed on a separate semiconductor die as MEMS transducer 102 and packaged together with MEMS transducer 102. Alternatively, ASIC 104 and MEMS transducer 102 may be formed on separate semiconductor dies and packaged in separate packages.

In various embodiments, processor 106 receives electronic signals from ASIC 104 based on transduced signals from MEMS transducer 102. In various embodiments, the electronic signals received at processor 106 from ASIC 104 are digital signals. In alternative embodiments, the electronic signals are analog signals. Processor 106 may be a specific application processor, a general microprocessor, a field programmable gate array (FPGA), or a central processing unit (CPU). In alternative embodiments, processor 106 is formed of discrete digital logic components. Processor 106 is attached to a same printed circuit board (PCB) as the package including ASIC 104 and MEMS transducer 102 in various embodiments.

Figure 2A:
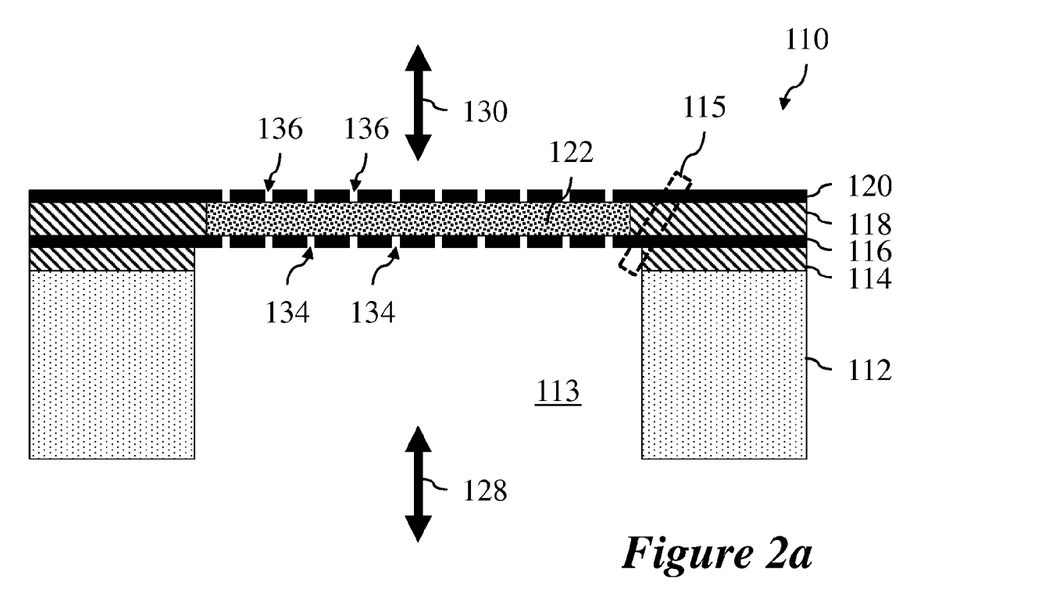
FIGS. 2a and 2b illustrate schematic cross-sectional views of embodiment MEMS gas sensors.
Figure 2B:
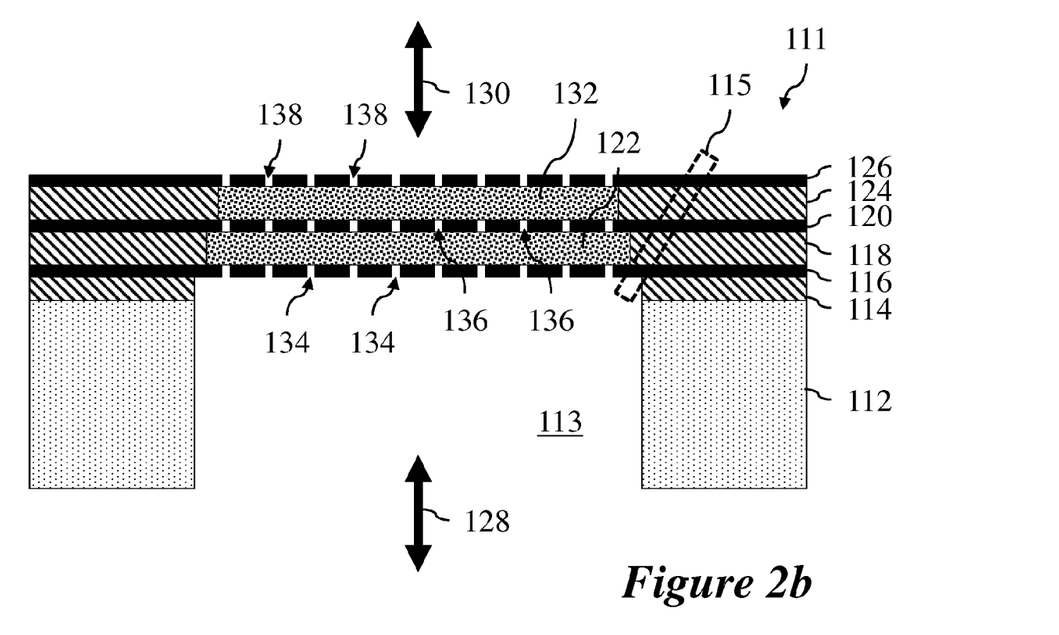

FIGS. 2a and 2b illustrate schematic cross-sectional views of embodiment MEMS gas sensors 110 and 111. MEMS gas sensor 110 includes substrate 112, first electrode 116, second electrode 120, and gas sensitive material 122 overlying cavity 113. According to various embodiments, gas sensitive material 122 is a dielectric that is sensitive to humidity. In such embodiments, as the humidity increases or decreases, the dielectric constant of gas sensitive material 122 changes accordingly. Based on the changes in dielectric constant, the parallel plate capacitance formed between first electrode 116 and second electrode 120 also changes. Such changes in capacitance may be measured by an interface circuit, such as ASIC 104, that is coupled to first electrode 116 and second electrode 120 through metallization layers (not shown).

In various embodiments, gas sensitive material 122 is in contact with the ambient environment of MEMS gas sensor 110. Because first electrode 116 and second electrode 120 encase gas sensitive material 122 from above and below, perforations 134 in first electrode 116 or perforations 136 in second electrode 120 provide openings that expose gas sensitive material 122 to the ambient environment. In such embodiments, perforations 134 and perforations 136 provide openings to receive environmental signals through environmental coupling 128 or environmental coupling 130, respectively. For example, environmental coupling 128 and environmental coupling 130 may be ports formed in the package that includes MEMS gas sensor 110.

In various embodiments, only one of environmental coupling 128, and corresponding perforations 134, or environmental coupling 130, and corresponding perforations 136, is included. In such embodiments, environmental coupling 130, and corresponding perforations 136, may correspond to a top port MEMS package. Similarly, environmental coupling 128, and corresponding perforations 134, may correspond to a bottom port MEMS package. In such embodiments, cavity 113 in substrate 112 is coupled to a bottom port in the MEMS package. In alternative embodiments, both environmental coupling 128, and corresponding perforations 134, and environmental coupling 130, and corresponding perforations 136, are included.

In various embodiments, structural layer 114 is formed on a top surface of substrate 112 and separates first electrode 116 from substrate 112. Further, structural layer 118 is formed on top of first electrode 116 and separates second electrode 120 from first electrode 116. In various embodiments, gas sensitive material 122 is structured above cavity 113 between first electrode 116 and second electrode 120 while structural layer 118 is structured above substrate 112 between first electrode 116 and second electrode 120. In alternative embodiments, structural layer 118 may be removed and gas sensitive material 122 may extend above substrate 112 between first electrode 116 and second electrode 120.

Gas sensitive material 122 is selected based on sensitivity to a certain gas concentration. Specifically, gas sensitive material 122 may be selected based on sensitivity to humidity. In various embodiments, gas sensitive material 122 may be selected for use in a resistance or capacitance based sensor and, therefore, may include materials that vary resistance or dielectric values based on the intended gas concentration. Some resistive materials may require operation at a higher temperature, i.e., may require a heater, in order to be sensitive to gas concentrations. In some embodiments, some dielectric gas sensitive materials may have a dielectric constant that is sensitive or proportional to a concentration of a specific gas without requiring heating to higher temperatures. In some embodiments, gas sensitive material 122 may be a polymer based material that varies capacitance, i.e., dielectric constant, based on humidity such as polyimide, polyesters, polymethyl methacrylate (PMMA), benzocyclobutene (BCB), polysulfates, and cellulose acetate butyrate. In other embodiments, gas sensitive material 122 may be a metal or semiconductor based material that varies capacitance, i.e., dielectric constant, based on humidity such as aluminum oxide, titanium oxide, silicon oxide, silicon carbide, or porous silicon. In other embodiments, gas sensitive material 122 may be a material that varies resistance based on humidity such as aluminum oxide, titanium oxide, or various spinels, e.g., $BaTiO_3$, $ZnCr_2O_4$, $K_2CrO_4$, and $MgAl_2O_4$.

In various other embodiments, gas sensitive material 122 may be selected to be sensitive to other gas concentrations. In specific embodiments, gas sensitive material 122 may be a material that varies capacitance, i.e., dielectric constant, based on gas concentration. In such embodiments, gas sensitive material 122 may be a ferroelectric material for sensing hydrogen; gas sensitive material 122 may be a fluoropolymer, CuO mixed with $BaSnO_3$, $SrTiO_3$, $CaTiO_3$, ZnO, or $BaTiO_3$ for sensing carbon dioxide; gas sensitive material 122 may be zirconium oxide or an iridium oxide for sensing oxygen; gas sensitive material 122 may be a tin dioxide for sensing ethylene; or gas sensitive material 122 may be porous silicon carbide or titanium oxide for sensing ammonia.

In still further specific embodiments, gas sensitive material 122 may be a material that varies resistance based on gas concentration. In such embodiments, gas sensitive material 122 may be a palladium based material for sensing hydrogen; gas sensitive material 122 may be $In_2Te_3$ for sensing carbon dioxide; gas sensitive material 122 may be zirconium oxide or an iridium oxide for sensing oxygen; gas sensitive material 122 may be a tin dioxide for sensing ethylene; or gas sensitive material 122 may be tin dioxide, tungsten oxide, various metal oxides, polypyrrole, or polyaniline for sensing ammonia.

In particular embodiments, it may be advantageous for gas sensitive material 122 to be formed of a material that is capable of being dispensed as a liquid or gel. In such embodiments, gas sensitive material may be applied post fabrication to a sensing region with two electrodes in order to form the MEMS gas sensor. In various other embodiments, gas sensitive material 122 may be formed of nanostructures, such as nanowires, for example.

According to some specific alternative embodiments, gas sensitive material 122 may be simply air. In such embodiments, the dielectric constant of air is dependent on the humidity, i.e., the amount of moisture in the air. Thus, the capacitance may be measured between first electrode 116 and second electrode 120 in order to determine changes in the dielectric constant of the air and, thereby, determine the changes in humidity.

According to various embodiments, substrate 112 may be a single element semiconductor substrate, such as silicon, germanium, carbon, or antimony. In other embodiments, substrate 112 may be a silicon-on-insulator (SOI) substrate, a III-V semiconductor substrate, or a II-VI semiconductor substrate. In some embodiments, substrate 112 may be glass. In alternative embodiments, substrate 112 may be a polymer substrate. In other alternative embodiments, substrate 112 may be a metal substrate.

According to various embodiments, first electrode 116 and second electrode 120 are formed of a conductive material. In specific embodiments, first electrode 116 and second electrode 120 are polysilicon. In some embodiments, first electrode 116 and second electrode 120 are aluminum, gold, or platinum. In one alternative embodiment, first electrode 116 and second electrode 120 are copper. In still another embodiment, first electrode 116 is silicon-on-insulator (SOI). In other embodiments, first electrode 116 and second electrode 120 may be formed of a doped semiconductor material. First electrode 116 and second electrode 120 may also be formed of a material stack including insulating layers that surround and encapsulate a conductive material. For example, a polysilicon layer may be encapsulated by silicon nitride to form first electrode 116 or second electrode 120.

In various embodiments, structural layer 114 and structural layer 118 are insulating materials. In some embodiments, structural layer 114 and structural layer 118 are an oxide, nitride, or oxynitride. In a specific embodiment, structural layer 114 and structural layer 118 are silicon oxide. In another specific embodiment, structural layer 114 and structural layer 118 are silicon nitride.

FIG. 2b shows MEMS gas sensor 111 including substrate 112, first electrode 116, second electrode 120, gas sensitive material 122, third electrode 126, and gas sensitive material 132 overlying cavity 113. MEMS gas sensor 111 includes elements as described in reference to MEMS gas sensor 110 with the addition of third electrode 126 and gas sensitive material 132. According to various embodiments, third electrode 126 is spaced apart from second electrode 120 by structural layer 124 and includes perforations 138. In such embodiments, one or both of environmental coupling 128 and environmental coupling 130 may be included in order to provide an environmental coupling between the ambient environment and MEMS gas sensor 111 from the top, the bottom (through cavity 113), or both. Gas sensitive material 132 may be any of the materials described in reference to gas sensitive material 122, third electrode 126 may be any of the materials or structures described in reference to first electrode 116 or second electrode 120, and structural layer 124 may be any of the materials or structures described in reference to structural layer 114 or structural layer 118.

In various embodiments, MEMS gas sensor 110 and MEMS gas sensor 111 may be formed of layers compatible with a single or double backplate capacitive microphone, respectively. In particular embodiments, the layers of MEMS gas sensor 110 and MEMS gas sensor 111 are formed using the same processing steps and layer stack as a single or double backplate capacitive microphone, respectively, with the addition of gas sensitive material 122 or gas sensitive material 132, as described further herein below in reference to the other figures.

According to various embodiments, MEMS gas sensor 110 and MEMS gas sensor 111 may include an integrated heating element that heats gas sensitive material 122 or gas sensitive material 132. For example, when gas sensitive material 122 is sensitive to humidity and MEMS gas sensor 110 operates as a humidity sensor, the integrated heating element may heat up gas sensitive material 122 to remove the moisture absorbed in gas sensitive material 122 and reset MEMS gas sensor 110. In specific embodiments, any of first electrode 116, second electrode 120, and third electrode 126 are configured as the integrated heating element. In alternative embodiments, an additional heating element (not shown) may be integrated on substrate 112 and thermally coupled to gas sensitive material 122 or gas sensitive material 132. In still more specific embodiments, the heating element may be in physical contact with gas sensitive material 122 or gas sensitive material 132. In some embodiments, first electrode 116, second electrode 120, or third electrode 126 may include patterned heating structures or elements (not shown) in the same device layer that are electrically insulated from the respective electrode.

In various embodiments, ventilation hole 115 passes through second electrode 120, structural layer 118, and first electrode 116 for MEMS gas sensor 110 or third electrode 126, structural layer 124, second electrode 120, structural layer 118, and first electrode 116 for MEMS gas sensor 111 and may serve as an access for both sides to the media coming in from either side through environmental coupling 128 or environmental coupling 130. In such embodiments, ventilation hole 115 may be a single ventilation hole or multiple ventilation holes in the sensing and structural layers that provides a path around the sensing structure for the media, e.g., gas, to contact gas sensitive material 122 or gas sensitive material 132 from both directions while including only one of environmental coupling 128 and environmental coupling 130. In some embodiments, ventilation hole 115 may also pass through gas sensitive material 122 or gas sensitive material 132. In still further embodiments, ventilation hole 115 may be formed in various layers or substrate 112 some distance from the gas sensor or cavity 113, but may still provide a bypass ventilation path.

Figure 3A:
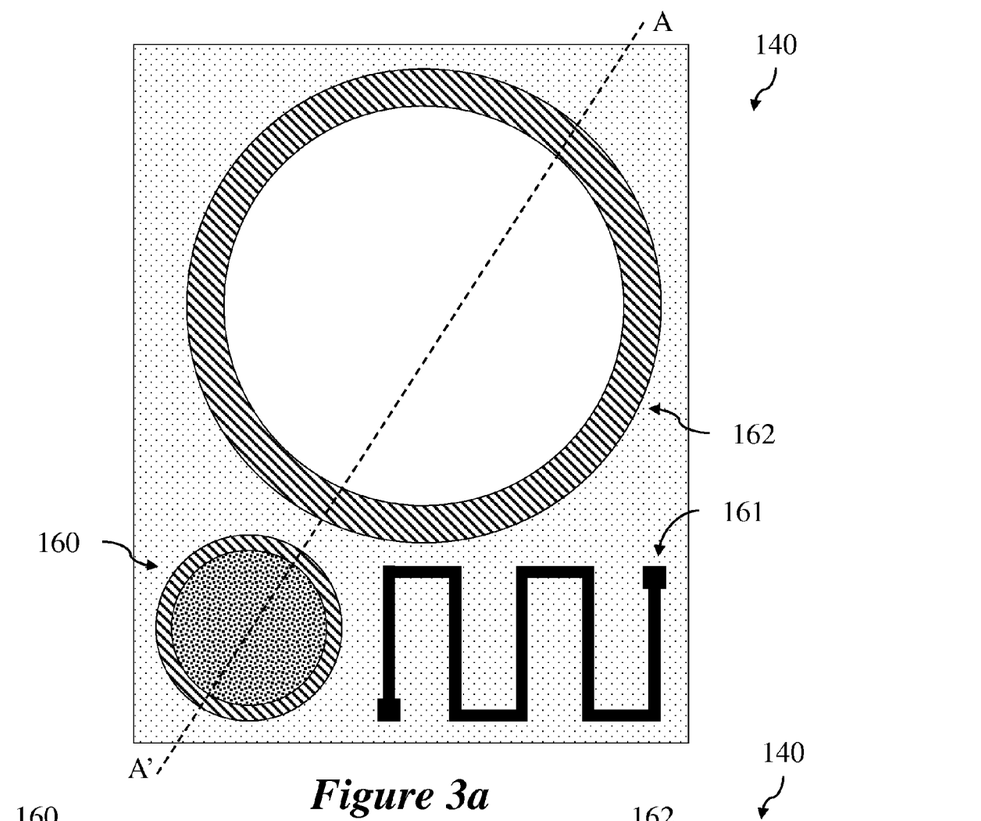
FIGS. 3a and 3b illustrate a top view and cross-sectional view of an embodiment integrated MEMS transducer.
Figure 3B:
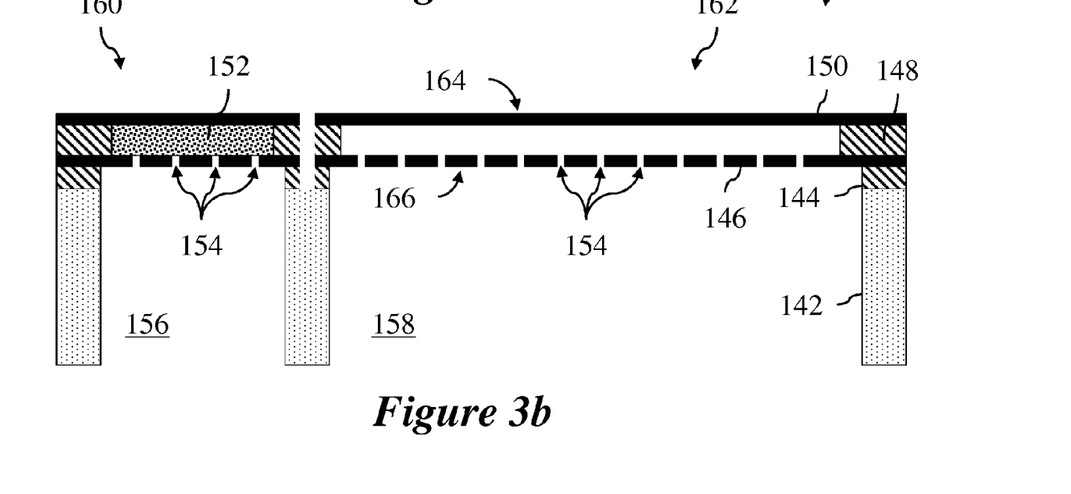

FIGS. 3a and 3b illustrate a top view and cross-sectional view of an embodiment integrated MEMS transducer 140 including gas sensor 160 and microphone 162. According to various embodiments, integrated MEMS transducer 140 is formed of top electrode layer 150 spaced apart from bottom electrode layer 146 by structural layer 148. Bottom electrode layer 146, structural layer 148, and top electrode layer 150 are spaced from substrate 142 by structural layer 144 and are formed overlying cavity 156 and cavity 158. In such embodiments, gas sensor 160 is a capacitive or resistive gas sensor as described hereinabove in reference to MEMS gas sensor 110 in FIG. 2a.

In various embodiments, gas sensor 160 includes gas sensitive material 152 over cavity 156 and microphone 162 includes deflectable membrane 164 and perforated backplate 166 over cavity 158. In such embodiments, deflectable membrane 164 and perforated backplate 166 are spaced apart by structural layer 148 and separated by an air gap over cavity 158. Deflectable membrane 164 is a part of, or formed by, top electrode layer 150 and perforated backplate 166 is a part of, or formed by, bottom electrode layer 146. Similarly, top electrode layer 150 forms the top electrode for gas sensor 160 and bottom electrode layer 146 forms the bottom electrode for gas sensor 160.

In other embodiments, microphone 162 may alternatively be a microspeaker. In some embodiments, microphone 162 may be implemented with a second perforated backplate and gas sensor 160 may also be implemented with a third electrode layer, as described in reference to MEMS gas sensor 111 in FIG. 2b. Although perforations are only shown in bottom electrode layer 146, perforations may be included in top electrode layer 150, depending on an environmental coupling or port (not shown), as described hereinabove in reference to perforations 134 and perforations 136 in FIGS. 2a and 2b. In various embodiments, cavity 156 and cavity 158 may be a same cavity or separate cavities in substrate 142. In such embodiments, cavity 156 and cavity 158 may be formed separately or simultaneously.

According to some embodiments, integrated MEMS transducer 140 further includes temperature sensing element 161. In such embodiments, temperature sensing element 11 may be include in or on substrate 142, or any of the layers of integrated MEMS transducer 140. Temperature sensing element 161 may be formed of any of the material described hereinabove in reference to first electrode 116 in FIG. 2a. In such embodiments, temperature sensing element 161 may be implemented as described in co-pending U.S. application Ser. No. 14/613,106, filed on Feb. 3, 2015, and entitled "System and Method for an Integrated Transducer and Temperature Sensor," which is incorporated herein in its entirety.

According to various embodiments, integrated MEMS transducer 140 may include an integrated heating element that heats gas sensitive material 152 as similarly described hereinabove in reference to MEMS gas sensor 110 and MEMS gas sensor 111 in FIGS. 2a and 2b. In such embodiments, the integrated heating element may be implemented using top electrode layer 150 or bottom electrode layer 146 in the region where either layer is in contact with gas sensitive material 152. In other alternative embodiments, a separate integrated heating structure (not shown) may be included on substrate 142 for heating gas sensitive material 152 as similarly described hereinabove in reference to MEMS gas sensor 110 and MEMS gas sensor 111 in FIGS. 2a and 2b.

According to various embodiments, the materials used for the structures in FIGS. 3a and 3b are the same as described in reference to corresponding structures in FIGS. 2a and 2b. Specifically, substrate 142 may include any of the materials or structures described in reference to substrate 112, structural layer 144 may include any of the materials or structures described in reference to structural layer 114, bottom electrode layer 146 may include any of the materials or structures described in reference to first electrode 116, structural layer 148 may include any of the materials or structures described in reference to structural layer 118, top electrode layer 150 may include any of the materials or structures described in reference to second electrode 120, and gas sensitive material 152 may include any of the materials or structures described in reference to gas sensitive material 122. Further, description of perforations 134 and perforations 138 also applies to perforations 154.

According to various embodiments, integrated MEMS transducer 140 includes both gas sensor 160 and microphone 162 in substrate 142. Thus, both gas sensor 160 and microphone 162 may be formed simultaneously using the same microfabrication sequence, with the addition of gas sensitive material 152, and integrated on the same semiconductor die.

In some embodiments, temperature sensing element 161 is also integrated on the same semiconductor die. Such embodiments may include components with increased functionality and a very small increase in fabrication cost and complexity.

Figure 4A:
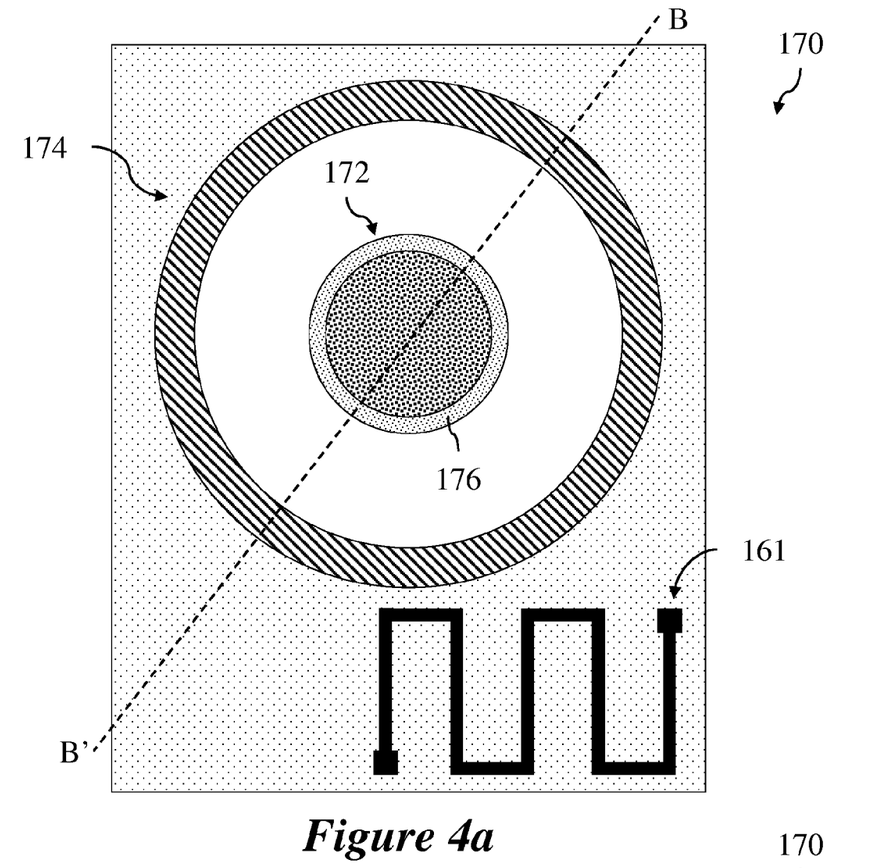
FIGS. 4a and 4b illustrate a top view and cross-sectional view of another embodiment integrated MEMS transducer.
Figure 4B:
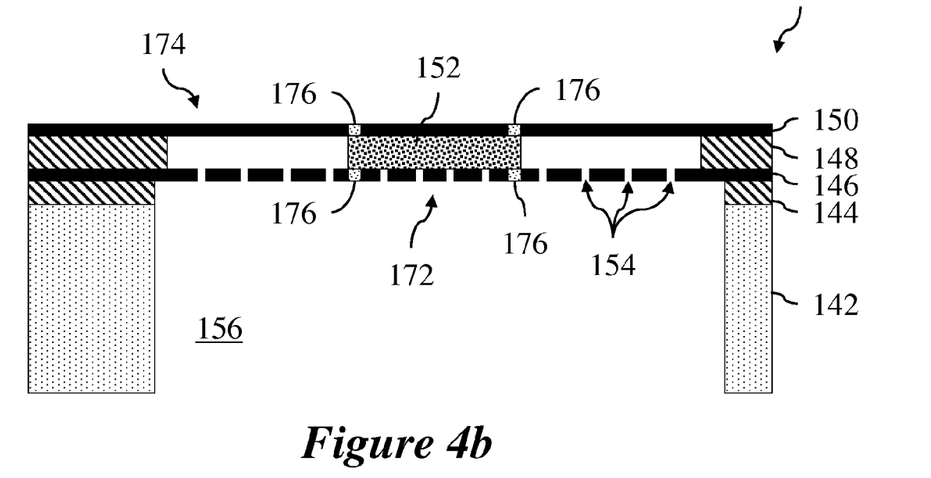

FIGS. 4a and 4b illustrate a top view and cross-sectional view of another embodiment integrated MEMS transducer 170 including gas sensor 172 and microphone 174. According to various embodiments, integrated MEMS transducer 170 is formed of top electrode layer 150 spaced apart from bottom electrode layer 146 by structural layer 148 as described in reference to integrated MEMS transducer 140 in FIGS. 3a and 3b. Gas sensor 172 is a capacitive or resistive gas sensor as similarly described hereinabove in reference to MEMS gas sensor 110 and gas sensor 160 in FIG. 2a and FIGS. 3a and 3b; with the exception that gas sensor 172 is integrated in a central region of microphone 174. In some embodiments, integrated MEMS transducer 170 includes temperature sensing element 161 as described hereinabove in reference to FIG. 3a. Microphone 174 may be microspeaker in some embodiments. Integrated MEMS transducer 170 may also include an integrated heating element as described hereinabove in reference to integrated MEMS transducer 140 in FIGS. 3a and 3b.

In such embodiments, gas sensitive material 152 is formed between top electrode layer 150 and bottom electrode layer 146 in a central released region overlying cavity 156. An air gap separates top electrode layer 150 and bottom electrode layer 146 in a region surrounding gas sensitive material 152. The region with the air gap and without gas sensitive material 152 includes a deflectable membrane portion, formed from top electrode layer 150, and a perforated backplate portion, formed from bottom electrode layer 146, which together operate as microphone 174. Thus, top electrode layer 150 and bottom electrode layer 146 form the sensing electrodes for both gas sensor 172 and microphone 174. In such embodiments, deflections of top electrode layer 150, as the deflectable membrane for microphone 174, occur in the portion surrounding gas sensitive material 152, while the region immediately above gas sensitive material 152 is fixed to gas sensitive material 152 and does not substantially deflect.

According to various embodiments, both top electrode layer 150 and bottom electrode layer 146 are segmented into two separate electrode regions in order to provide electrodes for both microphone 174 and gas sensor 172 in the same layer. Segmentation regions 176 provide segmentation of both top electrode layer 150 and bottom electrode layer 146. In various embodiments, segmentation regions 176 may be formed of an insulating material. In specific embodiments, segmentation regions 176 are formed of an oxide, nitride, or oxynitride. In other embodiments, segmentation regions 176 are formed only by removing portions of top electrode layer 150 and bottom electrode layer 146 in segmentation regions 176. In some alternative embodiments, segmentation regions 176 pass completely through gas sensitive material 152 and may form a continuous layer.

Further, electrical connections to the two separate electrode regions of both top electrode layer 150 and bottom electrode layer 146 are provided by metallization or doped semiconductors, for example (not shown). Such electrical connections generally include additional segmentation or insulation (not shown) formed on or in top electrode layer 150 and bottom electrode layer 146, as will be readily understood by one having ordinary skill in the art.

Figure 5A:
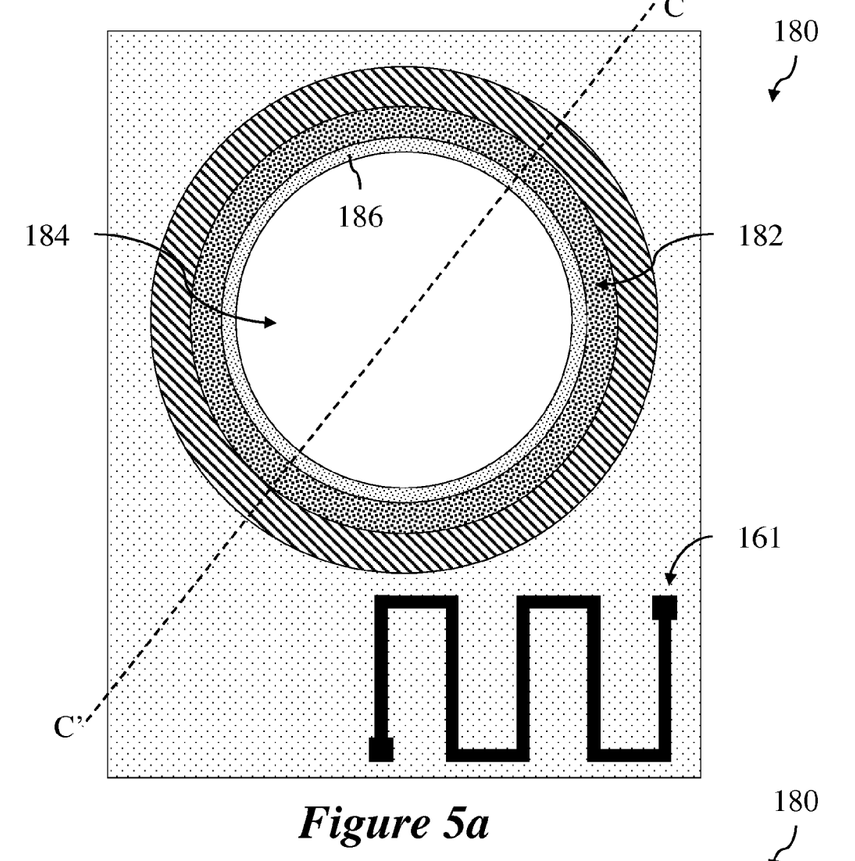
FIGS. 5a and 5b illustrate a top view and cross-sectional view of a further embodiment integrated MEMS transducer.
Figure 5B:
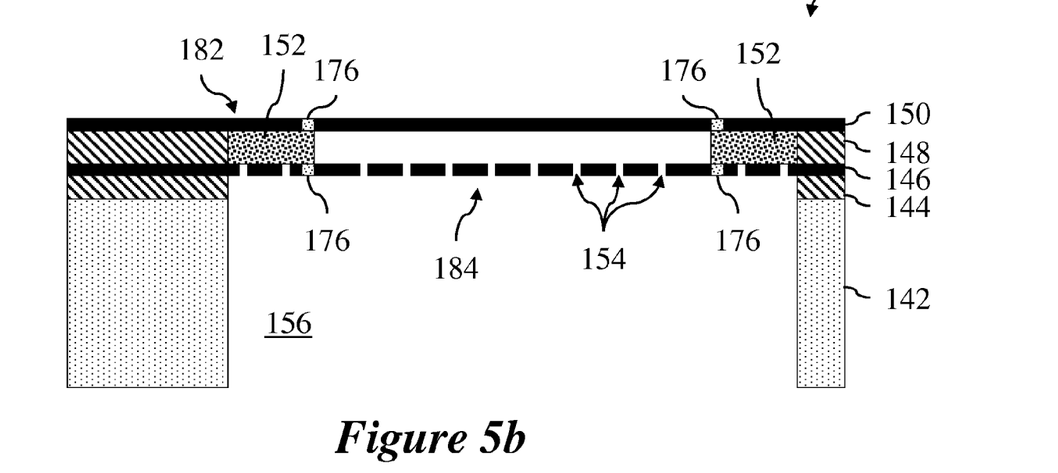

FIGS. 5a and 5b illustrate a top view and cross-sectional view of a further embodiment integrated MEMS transducer 180 including gas sensor 182 and microphone 184. According to various embodiments, integrated MEMS transducer 180 is similar to integrated MEMS transducer 170 described hereinabove in reference to FIGS. 4a and 4b; with the exception that gas sensor 182 is integrated in a peripheral region surrounding microphone 184.

In such embodiments, gas sensitive material 152 is formed in the peripheral region adjacent to structural layer 148 between top electrode layer 150 and bottom electrode layer 146 and above cavity 156. The central portion of top electrode layer 150 forms the deflectable membrane for microphone 184 and the central portion of bottom electrode layer 146 forms the perforated backplate for microphone 184. Similarly, the peripheral region of top electrode layer 150 and the peripheral region of bottom electrode layer 146 together form the top and bottom electrodes, respectively, for gas sensor 182. As described in reference to FIG. 4b, segmentation regions 176 in top electrode layer 150 and bottom electrode layer 146 separate the sensing electrodes for gas sensor 182 from the sensing electrodes, membrane and backplate, for microphone 184. In some embodiments, integrated MEMS transducer 180 includes temperature sensing element 161 as described hereinabove in reference to FIG. 3a. Microphone 184 may be microspeaker in some embodiments. Integrated MEMS transducer 180 may also include an integrated heating element as described hereinabove in reference to integrated MEMS transducer 140 in FIGS. 3a and 3b.

Figure 6A:
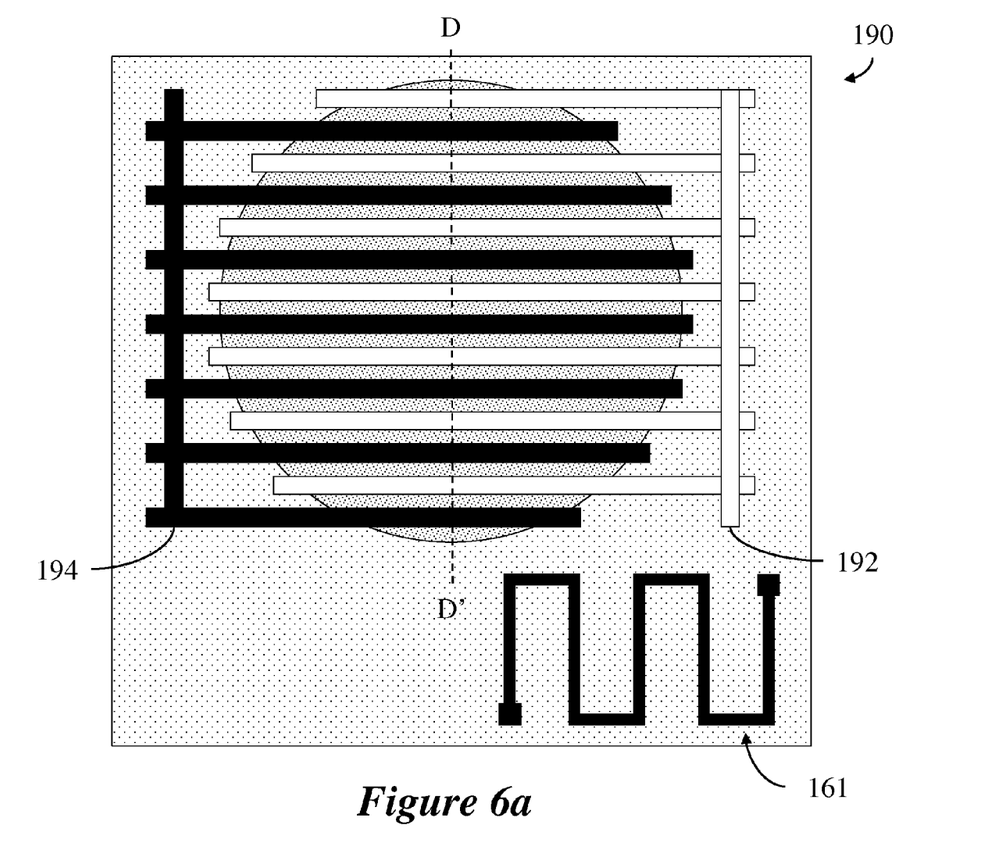
FIGS. 6a and 6b illustrate a top view and cross-sectional view of another embodiment MEMS gas sensor.
Figure 6B:
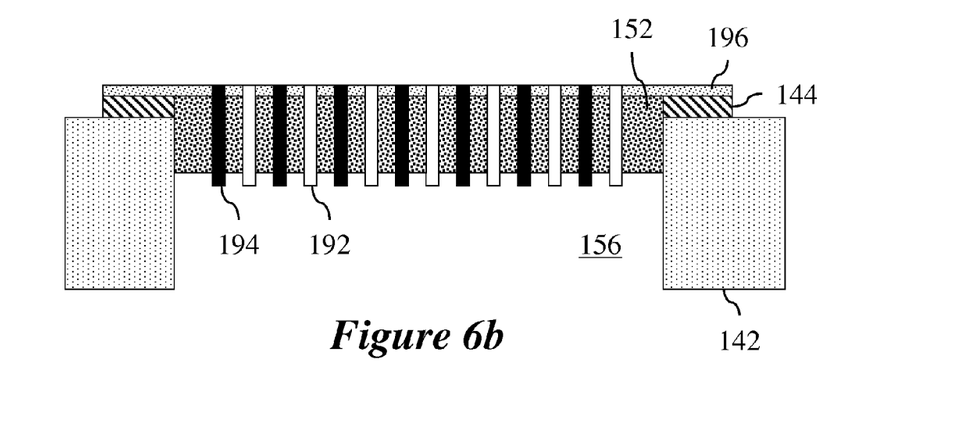

FIGS. 6a and 6b illustrate a top view and cross-sectional view of another embodiment MEMS gas sensor 190 including first interdigitated electrode 192 and second interdigitated electrode 194. According to various embodiments, first interdigitated electrode 192, second interdigitated electrode 194, and membrane layer 196 together form a structured membrane that has interdigitated electrodes filled with gas sensitive material 152 in the gaps between first interdigitated electrode 192 and second interdigitated electrode 194. As similarly described hereinabove, gas sensitive material 152 may be implemented as a material with a resistance value or dielectric constant that depends on a specific gas concentration. In such embodiments, first interdigitated electrode 192 and second interdigitated electrode 194 may function as electrodes for a resistive gas sensor or a capacitive gas sensor. Further description of interdigitated electrodes is included in co-pending U.S. application Ser. No. 13/743,306, filed Jan. 16, 2013, and entitled "Comb MEMS Device and Method of Making a Comb MEMS Device," which is incorporated herein by reference in its entirety, and in co-pending U.S. application Ser. No. 13/947,823, filed Jul. 22, 2013, and entitled "MEMS Device," which is incorporated herein by reference in its entirety. Various embodiments described herein may be combined with fabrication techniques for a comb drive or interdigitated electrode MEMS sensor in order to fabricate MEMS gas sensor 190. MEMS gas sensor 190 may also include an integrated heating element as described hereinabove in reference to integrated MEMS transducer 140 in FIGS. 3a and 3b or MEMS gas sensor 110 in FIG. 2a, for example.

In various embodiments, membrane layer 196 is spaced from substrate 142 by structural layer 144. First interdigitated electrode 192 and second interdigitated electrode 194 may be formed of conductive materials, such as described hereinabove in reference to first electrode 116 and second electrode 120 in FIG. 2a. Further, first interdigitated electrode 192 and second interdigitated electrode 194 are formed as ridges or fins that extend through membrane layer 196 and gas sensitive material 152. Membrane layer 196 may be formed of an insulating material, such as an oxide, nitride, or oxynitride. In other embodiments, membrane layer 196 is formed of the same material as first interdigitated electrode 192 and second interdigitated electrode 194 and additional segmentation of insulation (not shown) is included between first interdigitated electrode 192 and second interdigitated electrode 194.

Figure 7:
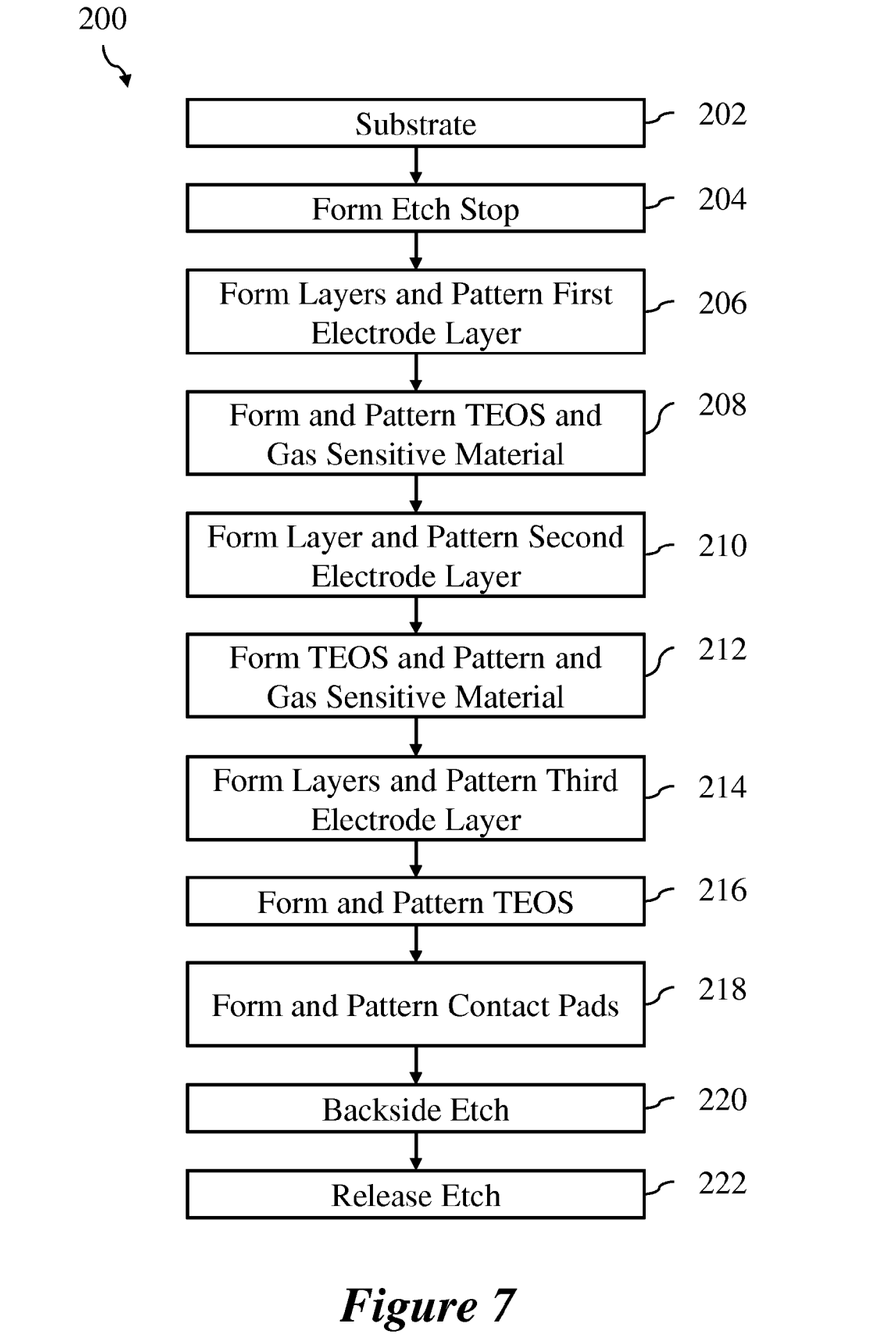
FIG. 7 illustrates a block diagram of an embodiment fabrication process for forming a MEMS transducer.

FIG. 7 illustrates a block diagram of an embodiment fabrication process 200 for forming a MEMS transducer, where fabrication process 200 includes steps 202-222. According to various embodiments, fabrication process 200 begins with a substrate in step 202. The substrate may be formed of a semiconductor, such as silicon, or as another material, such as a polymer for example. An etch stop layer is formed on the substrate in step 204. The etch stop layer may be silicon oxide formed using tetraethyl orthosilicate (TEOS), for example. In other embodiments, the etch stop layer may be silicon nitride.

In step 206, a first electrode layer is formed by forming and patterning layers for the first electrode layer. Step 206 may include depositing a single layer for the first electrode layer or multiple layers for the first electrode layer. As an example of multiple layers, step 206 may include depositing an insulating layer, such as SiN, depositing a conducting layer, such as polysilicon, patterning the conducting layer, depositing another insulating layer, such as SiN, and patterning the resulting stack of layers. Patterning may include a photolithographic process to produce the first electrode layer structure with perforations. As an example of a single layer, step 206 may include depositing a conducting layer, such as polysilicon, and patterning the conducting layer. In various embodiments, the first electrode layer may be any of the materials described hereinabove in reference to first electrode 116 in FIG. 2*a*. In some embodiments, step 206 also includes forming a temperature sensing element in or on the substrate or the first electrode layer, such as temperature sensing element 161 described hereinabove in reference to FIGS. 3*a* and 3*b*.

In other embodiments, structure variations and material alternatives are envisioned. In some alternative embodiments, the first electrode layer may be formed of any number of layers, conductive or insulating. For example, in some embodiments, the first electrode layer may include layers of metals, semiconductors, or dielectrics. In some embodiments, the first electrode layer may be formed of silicon on insulator (SOI) or metal and dielectric layers.

In various embodiments, step 208 includes forming and patterning a structural material, such as TEOS, and a gas sensitive material. Forming and patterning in step 208 is performed in order to provide spacing for a second electrode layer in a region for a MEMS microphone or microspeaker and to provide the gas sensitive material in a region for a MEMS gas sensor. In various embodiments, the first electrode layer and the second electrode layer may be part of a backplate and a membrane for the MEMS microphone or microspeaker and also part of a first electrode and a second electrode for the MEMS gas sensor, as described hereinabove in reference to the other figures. According to various embodiments, the gas sensitive material of step 208 may be patterned to form any of the gas sensors as described hereinabove in reference to the other figures. Further, the gas sensitive material of step 208 may include any of the materials described in reference to gas sensitive material 122 in FIG. 2*a*. The structural layer of step 208 may be patterned in order to form anti-stiction bumps for the second electrode layer. In addition, the structural layer formed in step 208 may include multiple depositions and a planarization step, such as a chemical mechanical polish (CMP).

Step 210 includes forming the second electrode layer and patterning the second electrode layer. The second electrode layer may be formed of polysilicon, for example. In other embodiments, the second electrode layer may be formed of other conductive materials, such as a doped semiconductor or a metal, for example. In various embodiments, the second electrode layer may be any of the materials described in reference to second electrode 120 in FIG. 2*a*. Patterning the second electrode layer in step 210 may include a photolithographic process, for example, that defines the shapes or structures of second electrodes for both a MEMS gas sensor and a MEMS microphone. The second electrode layer may include anti-stiction bumps in a region for the membrane of the microphone based on the structure formed in step 208.

In some embodiments, the step of forming the second electrode layer in step 210 may also include a step of forming a temperature sensing element formed in or on the same layer as the second electrode layer. According to various embodiments, only a single backplate microphone is formed and, therefore, only the first electrode layer and the second electrode layer are formed. In such embodiments, step 212 and step 214 may be omitted.

In various embodiments for forming a dual backplate microphone, step 212 includes forming and patterning additional structural material, such as TEOS, and a gas sensitive material. Similar to step 208, the structural material may be formed and patterned in step 212 to space a third electrode layer, which may form a second backplate, from the second electrode layer in a region for the MEMS microphone or microspeaker and the gas sensitive material may be formed and patterned in a region for the MEMS gas sensor. Step 212 may include depositing any of the materials described in reference to step 208. Step 214 includes forming and patterning the layers of the third electrode layer. In some embodiments, forming and patterning in step 214 includes deposition of layers and photolithographic patterning, for example. In various embodiments, step 214 may include similar features and materials as described hereinabove in reference to the first electrode layer formed in step 206 and the same description applies. Thus, in various embodiments, step 214 may also include forming a temperature sensing element.

Following step 214, step 216 includes forming and patterning additional structural material in various embodiments. The structural material may be a TEOS oxide. In some embodiments, the structural material is deposited as a sacrificial material or a masking material for subsequent etch or patterning steps. Step 218 includes forming and patterning contact pads. Forming and patterning the contact pads in step 218 may include etching contact holes in the existing layers to provide openings to the third electrode layer, the second electrode layer, first electrode layer, the substrate, and the temperature sensing element. In a specific embodiment, the temperature sensing element may have two openings for two contact pads that couple to the temperature sensing element.

After forming the openings to each respective structure or layer, the contact pads may be formed by depositing a conductive material, such as a metal, in the openings and patterning the conductive material to form separate contact pads. Step 218 may also include forming a temperature sensing element in metallization layers or between contact pads. For example, a resistive element with a resistance dependent on temperature may be formed between additional contact pads. In one specific embodiment, a platinum wire is formed between contact pads in step 218. In a still further embodiment, step 218 may also include forming a back contact for measuring a spreading resistance of the substrate.

In various embodiments, step 220 includes performing a backside etch, such as a Bosch etch. The backside etch forms a cavity in the substrate in order to form a sound port to the fabricated microphone and temperature sensor or to form a reference cavity. Step 222 includes performing a release etch to remove the structural materials protecting and securing the first electrode layer, the second electrode layer, and the third electrode layer. Following the release etch in step 222, the membrane, formed by a portion of the second electrode layer for example, of the microphone may be free to move in some embodiments.

Fabrication process 200 may be modified in specific embodiments to include only a single backplate and membrane for the integrated microphone. Those of skill in the art will readily appreciate that numerous modifications may be made to the general fabrication sequence described hereinabove in order to provide various benefits and modifications known to those of skill in the art while still including various embodiments of the present invention. In some embodiments, fabrication sequence 200 may be implemented to form a microspeaker having a similar structure as a single backplate MEMS microphone, for example. In other embodiments, fabrication sequence 200 may be implemented to form only a gas sensor and no integrated microphone. In various embodiments, fabrication sequence 200 may also include forming separate heating elements in contact with the gas sensitive material.

Figure 8:
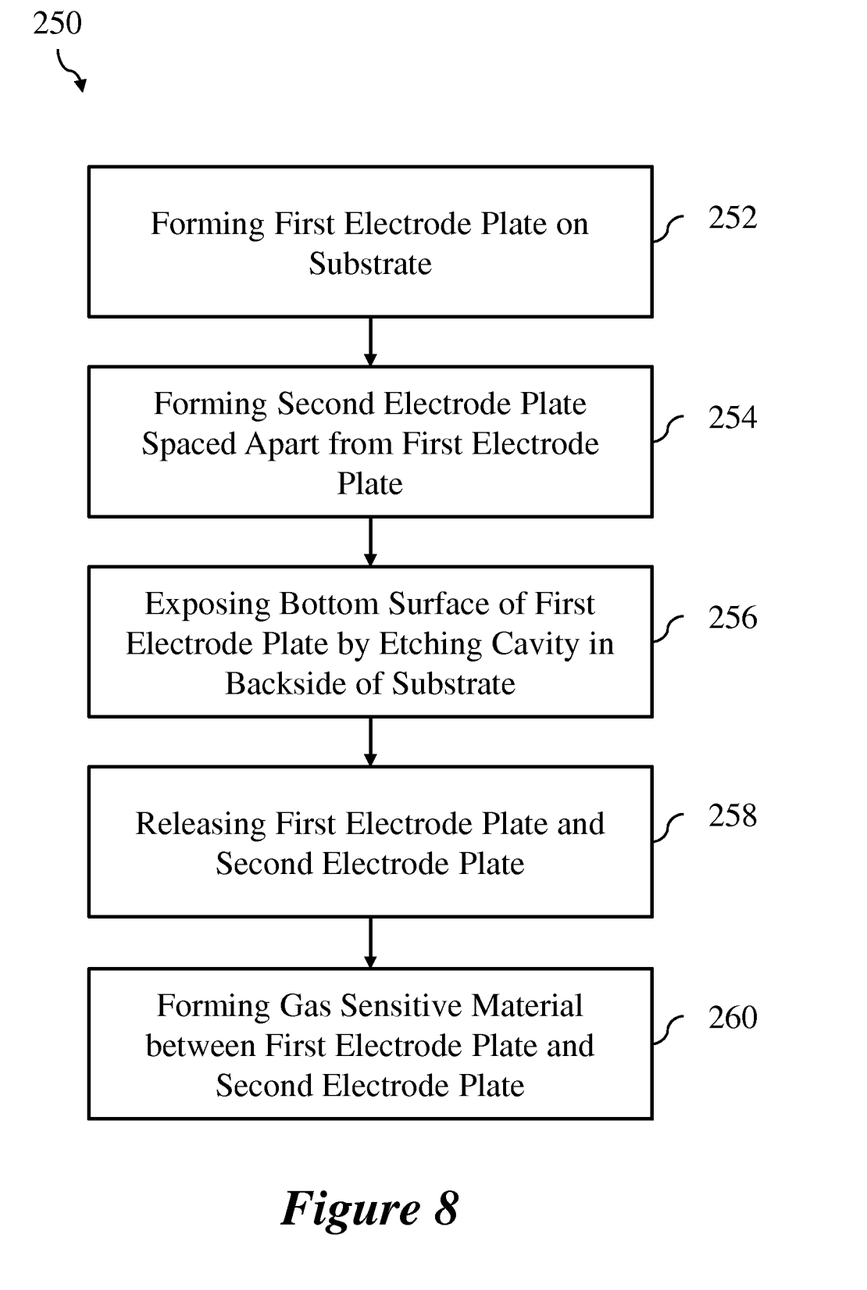
FIG. 8 illustrates a block diagram of another embodiment method of forming a MEMS transducer.

FIG. 8 illustrates a block diagram of another embodiment method of forming 250 a MEMS transducer, where method of forming 250 includes steps 252-260. According to various embodiments, step 252 includes forming a first electrode plate on a substrate. Step 254 includes forming a second electrode plate spaced apart from the first electrode plate. Step 256 includes exposing a bottom surface of the first electrode plate by etching a cavity in a backside of the substrate. The cavity may be connected to a port in a package for the MEMS transducer, where the port provides an opening, or coupling, to the ambient environment outside of and surrounding the package.

In various embodiments, step 258 includes releasing the first electrode plate and the second electrode plate. After release, the first electrode plate and the second electrode plate are released from below, in the cavity, and above. In such embodiments, the first electrode plate and the second electrode plate may still be connected by a gas sensitive material formed (in step 260) between the first and second electrode plates, for example, as described hereinabove in reference to FIGS. 2a, 2b, 3a, 3b, 4a, 4b, 5a, 5b, 6a, and 6b, for example.

According to various embodiments, step 260 includes forming a gas sensitive material on the first electrode plate. In some embodiments, the gas sensitive material is a gas sensitive dielectric material that has a dielectric constant that varies in relation to the concentration of a specific gas. For example, the gas sensitive dielectric material has a dielectric constant that varies with humidity, i.e., the concentration of water vapor in the air. The gas sensitive dielectric material may instead be a resistive material as described hereinabove in reference to the other figures.

In further embodiments, method of forming 250 may include additional steps in different orders. For example, method of forming 250 may include additional steps for forming a third electrode plate. In some embodiments, a microphone is formed during the same steps 252-260 for the MEMS transducer. Thus, a gas sensor and a microphone are formed simultaneously using the same electrode layers. In still further embodiments, a temperature sensing element is also formed during method of forming 250.

According to various embodiments, step 260 may be performed at the end of method of forming 250 as a post-processing step. In such embodiments, the gas sensitive material, as a dielectric or a resistive material, is dispensed, printed, or applied to the released MEMS system. In some embodiments, the gas sensitive material may be applied only to sensing areas, e.g., not to a microphone portion, as described hereinabove in reference to FIGS. 2 and 3. In other embodiments, the gas sensitive material may be applied to a capacitive plate sensor within specific gas sensor portions separated from acoustic transducer portions as described hereinabove in reference to FIGS. 4 and 5. In still other embodiments, the gas sensitive material may be applied to interdigitated electrodes as described hereinabove in reference to FIG. 6. In such embodiments, the post-processing filling with gas sensitive material may be applied such that capillary forces fill the gaps between interdigitated electrodes with gas sensitive material and the applied amount of gas sensitive material limits the filling volume between the gaps. In other embodiments, step 260 is performed between step 252 and step 254 and includes depositing the gas sensitive material on top of the first electrode plate before forming the second electrode plate.

According to an embodiment, a microelectromechanical systems (MEMS) transducer includes a substrate with a first cavity that passes through the substrate from a backside of the substrate. The MEMS transducer also includes a perforated first electrode plate overlying the first cavity on a topside of the substrate, a second electrode plate overlying the first cavity on the topside of the substrate and spaced apart from the perforated first electrode plate by a spacing region, and a gas sensitive material in the spacing region between the perforated first electrode plate and the second electrode plate. The gas sensitive material has an electrical property that is dependent on a concentration of a target gas. Other embodiments include corresponding systems and apparatus, each configured to perform corresponding embodiment methods.

Implementations may include one or more of the following features. In various embodiments, the MEMS transducer further includes a MEMS acoustic transducer integrated on the substrate, where the MEMS acoustic transducer includes a perforated backplate overlying a second cavity in the substrate, and a deflectable membrane overlying the second cavity and spaced apart from the perforated backplate. In some embodiments, the perforated backplate is formed of a same semiconductor layer as the perforated first electrode plate, and the deflectable membrane is formed of a same semiconductor layer as the second electrode plate. The first cavity and the second cavity may be a same cavity that passes through the substrate from a backside of the substrate.

In various embodiments, the perforated first electrode plate includes a central portion of the perforated backplate and the second electrode plate includes a central portion of the deflectable membrane. In other embodiments, the perforated first electrode plate includes a peripheral portion of the perforated backplate and the second electrode plate includes a peripheral portion of the deflectable membrane.

In various embodiments, the target gas is water vapor and the gas sensitive material is a humidity sensitive material. In specific embodiments, the humidity sensitive material is polyimide. In other embodiments, the target gas is carbon dioxide.

In various embodiments, the MEMS transducer further includes a perforated third electrode plate overlying the first cavity on the topside of the substrate and spaced apart from the second electrode plate by an additional spacing region, and also further includes the gas sensitive material in the additional spacing region between the perforated third electrode plate and the second electrode plate. The perforated first electrode plate may be coupled to an ambient environment through the first cavity and a port in a package containing the MEMS transducer. In some embodiments, the perforated first electrode plate overlies the second electrode plate and is coupled to an ambient environment through a top port in a package containing the MEMS transducer.

In various embodiments, the MEMS transducer further includes a temperature sensing element integrated on the substrate. The MEMS transducer may further include a heating element in physical contact with the gas sensitive material. In some embodiments, the MEMS transducer further includes a ventilation opening that bypasses the perforated first electrode plate and the second electrode plate and provides a ventilation path between the first cavity and the topside of the substrate. According to various embodiments, the gas sensitive material includes a gas sensitive dielectric material that has a dielectric constant that is dependent on the concentration of the target gas.

According to an embodiment, a method of fabricating a MEMS sensor includes forming a first electrode plate on a substrate, forming a second electrode plate spaced apart from the first electrode plate, exposing a bottom surface of the first electrode plate by etching a cavity in a backside of the substrate, releasing the first electrode plate and the second electrode plate, and forming a gas sensitive material between the first electrode plate and the second electrode plate. Other embodiments include corresponding systems and apparatus, each configured to perform corresponding embodiment methods.

Implementations may include one or more of the following features. In various embodiments, forming the gas sensitive material includes dispensing the gas sensitive material as a liquid into a region between the first electrode plate and the second electrode plate after releasing the first electrode plate and the second electrode plate. Dispensing the gas sensitive material as a liquid may include dispensing polyimide as a liquid. In other embodiments, forming the gas sensitive material includes depositing the gas sensitive material on the first electrode plate before forming the second electrode plate.

In various embodiments, the gas sensitive material includes a gas sensitive dielectric material with a dielectric constant that is proportional to a concentration of a target gas. In some embodiments, forming the first electrode plate includes forming a perforated first electrode plate. Forming the perforated first electrode plate on the substrate may also include forming a perforated backplate, forming the gas sensitive material may include forming the gas sensitive material in a first region over the perforated backplate and forming an air gap in a second region over the perforated backplate, and forming the second electrode plate on the gas sensitive material may further include forming a deflectable membrane over the air gap in the second region. In some embodiments, the first region is a peripheral region and the second region is a central region. In other embodiments, the second region is a peripheral region and the first region is a central region.

In various embodiments, the method further includes forming a perforated backplate simultaneous to forming the perforated first electrode plate, where the perforated backplate and the perforated first electrode plate are formed of a same semiconductor layer. In such embodiments, the method also further includes forming a deflectable membrane simultaneous to forming the second electrode plate, where the deflectable membrane and the second electrode plate are formed of a same semiconductor layer and the deflectable membrane is spaced apart from the perforated backplate. In some embodiments, the method further includes forming a heating element thermally coupled to the gas sensitive material. The method may also further include forming a temperature sensing element on the substrate.

According to an embodiment, a MEMS transducer includes a MEMS acoustic transducer that includes a perforated backplate overlying a substrate and a membrane overlying the substrate and spaced apart from the perforated backplate by a first spacing. The MEMS transducer further includes a MEMS gas sensor that includes a perforated first electrode overlying the substrate, a second electrode overlying the substrate and spaced apart from the perforated first electrode by a second spacing, and a gas sensitive dielectric between and in contact with the perforated first electrode and the second electrode. Other embodiments include corresponding systems and apparatus, each configured to perform corresponding embodiment methods.

Implementations may include one or more of the following features. In various embodiments, the perforated backplate and the perforated first electrode are formed of a same semiconductor layer. The substrate may include a cavity, and the perforated first electrode, the second electrode, and the gas sensitive dielectric overly the cavity. In some embodiments, the MEMS transducer further includes a temperature sensing element integrated on the substrate. In further embodiments, the MEMS transducer also includes a heating element in physical contact with the gas sensitive dielectric.

In various embodiments, the perforated first electrode is formed in a central region of the perforated backplate and the second electrode is formed in a central region of the membrane. In other embodiments, the perforated first electrode is formed in a peripheral region of the perforated backplate and the second electrode is formed in a peripheral region of the membrane.

According to some embodiments described herein, advantages may include adding functionality to an integrated product. Some embodiments may include an acoustic transducer and a gas sensor integrated in a same semiconductor die with shared functional device layers, such as electrode layers. Such embodiments may advantageously include no extra masks or only a single extra mask during the fabrication sequence when compared to an equivalent microphone fabrication sequence. Another advantage of some embodiments may include integrated temperature sensing functionality. Integration in a single semiconductor may also advantageously lead to improved performance and decreased cost in some embodiments. A further advantage of some embodiments may include providing environmental coupling for a group of sensors through a single hole or port, or shared holes or ports, in a single package. Such embodiments may advantageously improve performance, increase interchangeability of sensor systems, and simplify design constraints.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A microelectromechanical systems (MEMS) transducer comprising:
a substrate comprising a first cavity that passes through the substrate from a backside of the substrate;
a perforated first electrode plate overlying the first cavity on a topside of the substrate;
a second electrode plate overlying the first cavity on the topside of the substrate and spaced apart from the perforated first electrode plate by a spacing region;
a gas sensitive material in the spacing region between the perforated first electrode plate and the second electrode plate, wherein the gas sensitive material has an electrical property that is dependent on a concentration of a target gas; and
a MEMS acoustic transducer integrated on the substrate, the MEMS acoustic transducer comprising a perforated backplate overlying a second cavity in the substrate, and a deflectable membrane overlying the second cavity and spaced apart from the perforated backplate.

2. The MEMS transducer of claim 1, wherein
the perforated backplate is formed of a same semiconductor layer as the perforated first electrode plate; and
the deflectable membrane is formed of a same semiconductor layer as the second electrode plate.

3. The MEMS transducer of claim 2, wherein the first cavity and the second cavity are a same cavity that passes through the substrate from a backside of the substrate.

4. The MEMS transducer of claim 3, wherein the perforated first electrode plate comprises a central portion of the perforated backplate and the second electrode plate comprises a central portion of the deflectable membrane.

5. The MEMS transducer of claim 3, wherein the perforated first electrode plate comprises a peripheral portion of the perforated backplate and the second electrode plate comprises a peripheral portion of the deflectable membrane.

6. The MEMS transducer of claim 1, wherein the target gas is water vapor and the gas sensitive material is a humidity sensitive material.

7. The MEMS transducer of claim 6, wherein the humidity sensitive material is polyimide.

8. The MEMS transducer of claim 1, wherein the target gas is carbon dioxide.

9. The MEMS transducer of claim 1, further comprising:
a perforated third electrode plate overlying the first cavity on the topside of the substrate and spaced apart from the second electrode plate by an additional spacing region; and
the gas sensitive material in the additional spacing region between the perforated third electrode plate and the second electrode plate.

10. The MEMS transducer of claim 1, wherein the perforated first electrode plate is coupled to an ambient environment through the first cavity and a port in a package containing the MEMS transducer.

11. The MEMS transducer of claim 1, wherein the perforated first electrode plate overlies the second electrode plate and is coupled to an ambient environment through a top port in a package containing the MEMS transducer.

12. The MEMS transducer of claim 1, further comprising a temperature sensing element integrated on the substrate.

13. The MEMS transducer of claim 1, further comprising a heating element in physical contact with the gas sensitive material.

14. The MEMS transducer of claim 1, further comprising a ventilation opening that bypasses the perforated first electrode plate and the second electrode plate and provides a ventilation path between the first cavity and the topside of the substrate.

15. The MEMS transducer of claim 1, wherein the gas sensitive material comprises a gas sensitive dielectric material that has a dielectric constant that is dependent on the concentration of the target gas.

16. A microelectromechanical systems (MEMS) transducer comprising:
a MEMS acoustic transducer comprising:
a perforated backplate overlying a substrate, and
a membrane overlying the substrate and spaced apart from the perforated backplate by a first spacing; and
a MEMS gas sensor comprising:
a perforated first electrode overlying the substrate,
a second electrode overlying the substrate and spaced apart from the perforated first electrode by a second spacing, and
a gas sensitive dielectric between and in contact with the perforated first electrode and the second electrode.

17. The MEMS transducer of claim 16, wherein the perforated backplate and the perforated first electrode are formed of a same semiconductor layer.

18. The MEMS transducer of claim 16, wherein the substrate comprises a cavity and the perforated first electrode, the second electrode, and the gas sensitive dielectric overly the cavity.

19. The MEMS transducer of claim 16, further comprising a temperature sensing element integrated on the substrate.

20. The MEMS transducer of claim 16, further comprising a heating element in physical contact with the gas sensitive dielectric.

21. The MEMS transducer of claim 16, wherein
the perforated first electrode is formed in a central region of the perforated backplate; and
the second electrode is formed in a central region of the membrane.

22. The MEMS transducer of claim 16, wherein
the perforated first electrode is formed in a peripheral region of the perforated backplate; and
the second electrode is formed in a peripheral region of the membrane.

* * * * *